(12) United States Patent
Tripp et al.

(10) Patent No.: US 6,312,395 B1
(45) Date of Patent: Nov. 6, 2001

(54) CELL COLLECTION AND TRANSPORT

(75) Inventors: Patricia D. Tripp, Bluefield, VA (US); Kathleen M. Belcher, Mount Juliet, TN (US)

(73) Assignee: Innovative Genetic Technology, Bluefield, VA (US)

( * ) Notice: Subject to any disclaimer, the term of this patent is extended or adjusted under 35 U.S.C. 154(b) by 0 days.

(21) Appl. No.: 09/342,693

(22) Filed: Jun. 29, 1999

(51) Int. Cl.[7] .................................................. A61B 5/00
(52) U.S. Cl. ............................................................ 600/572
(58) Field of Search ........................ 600/562, 569–572; 604/1

(56) References Cited

U.S. PATENT DOCUMENTS

| | | | |
|---|---|---|---|
| 3,776,220 | 12/1973 | Monaghan | 128/2 |
| 3,890,204 | * 6/1975 | Avery | 600/572 |
| 4,150,950 | * 4/1979 | Takeguchi et al. | 600/572 |
| 4,175,008 | 11/1979 | White | 435/295 |
| 4,211,323 | 7/1980 | Olsen | 206/210 |
| 4,260,570 | * 4/1981 | Ravel | 604/1 |
| 4,409,988 | * 10/1983 | Greenspan | 600/572 |
| 4,472,357 | * 9/1984 | Levy et al. | 422/102 |
| 4,586,604 | 5/1986 | Alter | 206/210 |
| 5,084,005 | * 1/1992 | Kachigian | 600/569 |
| 5,085,633 | * 2/1992 | Hanifl et al. | 604/1 |
| 5,101,970 | 4/1992 | Turner | 206/223 |
| 5,211,286 | 5/1993 | Turner | 206/223 |
| 5,695,930 | 12/1997 | Weinstein et al. | 435/5 |
| 5,735,808 | 4/1998 | Delgado et al. | 604/1 |
| 5,736,325 | 4/1998 | Manowitz et al. | 435/6 |
| 5,830,154 | * 11/1998 | Goldstein et al. | 600/573 |
| 5,856,102 | 1/1999 | Bierke-Nelson et al. | 435/6 |

OTHER PUBLICATIONS

Photos of Micro Diagnostics, Inc. Swab Kit; date unknown but believed to be prior art.

* cited by examiner

Primary Examiner—Max Hindenburg
(74) Attorney, Agent, or Firm—Womble Carlyle Sandridge & Rice, PLLC

(57) ABSTRACT

The present invention discloses an apparatus for the collection and transportation of cell specimens comprising a polypropylene shaft, a dental foam swab formed in the shape of a multi-apexed polygon affixed to one end of the shaft, and a polypropylene cap affixed to the other end of the shaft. The cap is matingly engageable with a polypropylene tube proportioned to house the shaft and swab. Preferably, approximately 75% of the surface area of the cap is vented. Preferably, a tamper-evident seal is adhered about the engagement of the cap and tube and coordinated bar-coded labels are affixed to the cap and tube.

22 Claims, 4 Drawing Sheets

CELL COLLECTION AND TRANSPORT

FIELD OF THE INVENTION

This invention relates to the collection and transportation of cell cultures or specimens and more particularly to the collection and transportation of buccal cell cultures in an appropriate manner to maintain sterility before use, insure proper environmental conditions for the culture, and redress confusion among cultures.

BACKGROUND OF THE INVENTION

For a variety of reasons, different cell samples are taken from a selected area of a patient's body and transported to a laboratory facility for subsequent testing and identification. The testing may be related to diagnosis and treatment of illness or DNA research for, among other things, paternity or transplant matching. In the most common use, individual cotton-tipped swabs are prepackaged within paper envelopes. When taking a cell culture or specimen, the swab is removed from the envelope and applied or rubbed against the selected tissue area. The sample is then returned to the envelope and transported to the testing facility. For example, conventionally, buccal samples are collected by abrading the buccal lining with either a cotton-tipped swab, a disposable toothbrush or with one of a number of commercial collection devices. Then, the samples are transported to the testing facility in generic envelopes, plastic bags or plastic storage tubes.

There are several problems with the above-identified method of cell collection. First, conventional transportation devices do not maintain maximum sterility either before or after culture collection. In addition to the unprofessional appearance, unwanted contamination may result from inadvertent handling of the swab while placing it within the transport device. A collection swab should be able to obtain samples from tight areas without introduction of additional contaminants that would provide inaccurate testing results. The sample should then be transported from the collection site to the testing facility without damage or contamination. Additional problems with conventional transport devices include removal and loss of specimen onto the device and inadequate storage of the sample to maintain its effectiveness.

For DNA sampling, the samples must be allowed to sufficiently dry to prevent fungal and bacterial contamination. Thus, conventional devices are manipulated to accommodate drying. Envelopes and bags remain open and unsealed resulting in loss or contamination. Plastic tubes may be drilled or perforated, but the tip is still subjected to contamination.

The cotton swab, itself, is also inefficient and imperfect in collecting the culture. The design of the cotton swab does not allow for the natural variations that occur when taking the sample, such as the concentration and virility of the affected cells in the area for collection. Also, the use of natural fibers, cotton-tipped swab on a wooden stem, present additional contaminants that may be released onto sample surfaces.

Lastly, there is no assurance that the collector swab and the paper envelope are coordinated. In other words, without any pre-designated label, the paper envelope and swab may become separated. Conventional sampling devices are difficult to label effectively and consistently. In a worse-case scenario, cells may be collected from two separate samples and returned to respective envelopes. Some of the specimen may wipe off onto the envelope. Thereafter, the collector swabs may become separated from their respective envelopes and switched resulting in contaminated and effectively useless culture specimens.

There remains a need in the art for a cost-effective cell collection and transport apparatus that overcomes the above-stated problems.

SUMMARY

The present invention overcomes the short-comings of the prior art with an improved cell collection and transport apparatus. The apparatus generally comprises: (1) a polystyrene shaft; (2) a dental foam swab affixed to one end of the shaft; and (3) a polypropylene cap affixed to the other end of the shaft. The cap is matingly engageable with a polypropylene tube proportioned to house the shaft and swab. For buccal cell collection, the foam swab preferably is formed in the shape of a multi-pointed star. If cells are collected for DNA testing, preferably approximately 75% of the surface area of the cap should be vented for proper drying and extraction of the DNA. A tamper-evident seal is affixed about the line of engagement between the cap and tube; and coordinated labels are affixed to the cap and tube.

In this manner, the present invention provides a cost-effective collection and transport apparatus that minimizes contamination, minimizes mix-up between the collection member and the transport member and efficiently collects and protects collected cells.

DESCRIPTION OF THE PREFERRED EMBODIMENT

Figure 1:
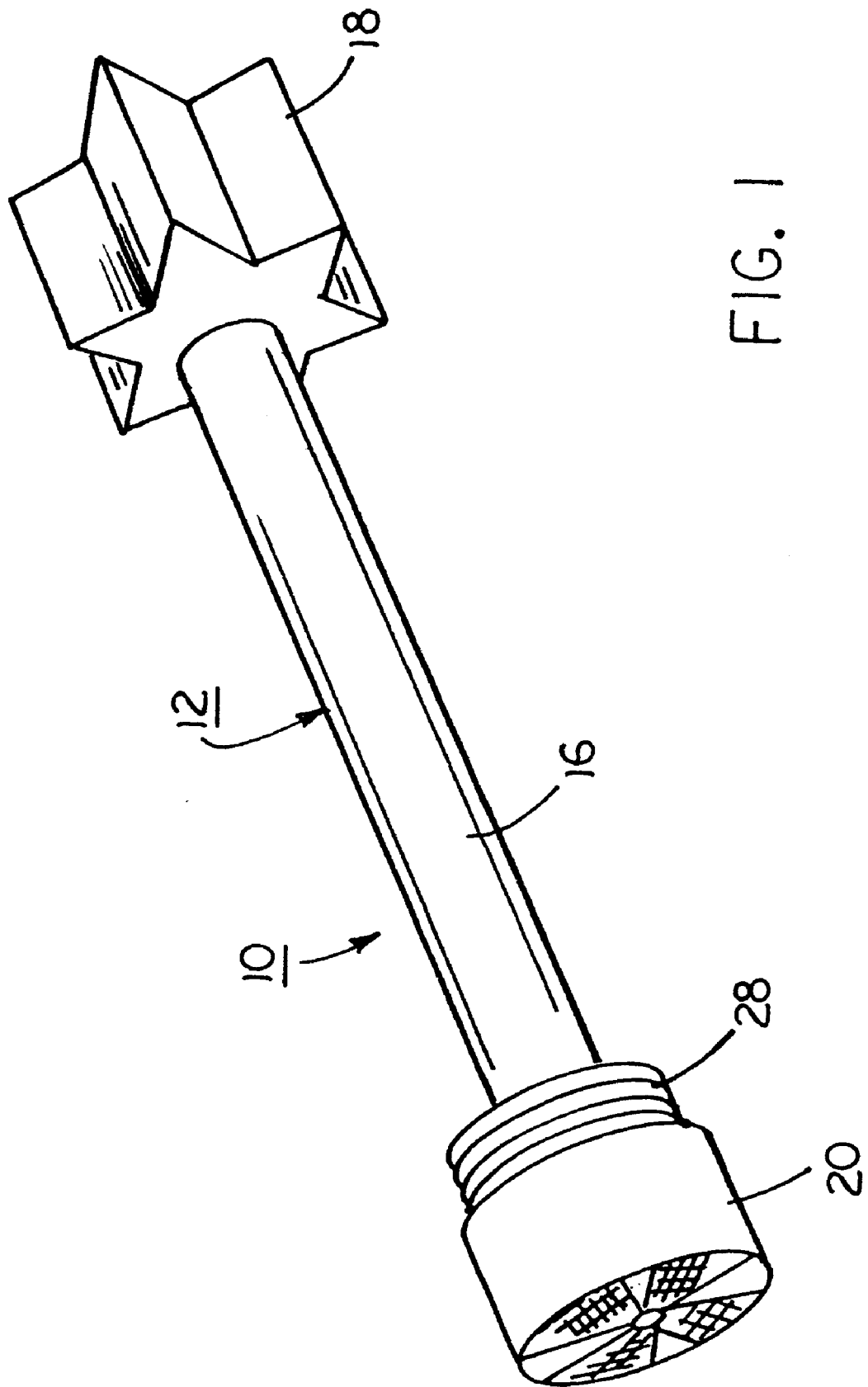
FIG. 1 is a perspective view of one embodiment of the cell collection component of the present invention.

As shown in the drawings, the present invention is a cell collection and transport apparatus 10. The combined apparatus is comprised, generally, of two components: a collection member 12 and a transport member 14.

The collection member 12 has a shaft 16 formed of any appropriate material, but preferably formed of polystyrene. Polystyrene is preferred because it is non-organic in nature and provides sufficient rigidity to aid in the scraping action required to abrade buccal cells. One end of the shaft 17 is covered with a swab 18 formed of any appropriate collector material. As discussed above, although a cotton swab is prevalent in the prior art, the preferred material is open cell polypropylene foam, such as USDA-approved dental foam, for example that sold under the tradename/trademark TOOTHETTE, by Sage Products of Crystal Lake, Illinois. The present invention envisions various shapes and sizes for the swab 18, however, a multiple-sided, multiple-apexed swab, for example a polygonal or multi-pointed star-shaped swab as shown in FIG. 5, is preferred because of the increased surface area and increased edges for abrading the buccal lining are provided. The preferred material and shape for the swab 18 is fashioned toward collection of buccal cells. The swab 18 should be secured to the shaft 16 through appropriate means, such as chemical welding, to prevent detachment.

Figure 4:
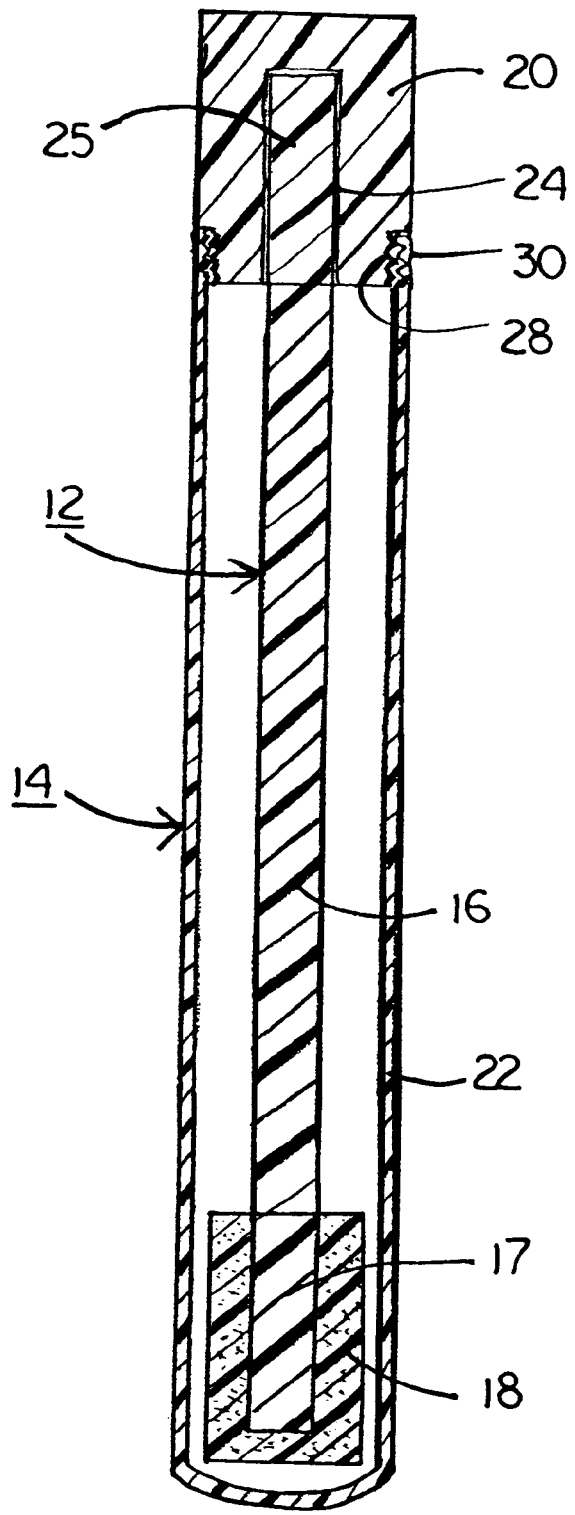
FIG. 4 is a side cross-sectional view of one embodiment of the present invention.

Preferably, to ensure coordination and connection between the collection member 12 and the transport member 14, the shaft 16 of the collection member is affixed to the cap 20 of the transport member. The cap 20 and tube 22 of the transport member 14 may be formed of any appropriate materials with polypropylene being preferred because of the resistance to breakage of polypropylene and the superior seal provided when secured to the polypropylene transport member 14. Thus, the inside area of the cap 20 should be appropriately formed to receive the shaft 16. For example, as shown in FIG. 4, the cap 20 may be molded with an inner sleeve 24 formed to receive the second end of the collection member shaft 25. The second end 25 of the shaft 16 should be secured to the cap 20 through any appropriate means, such as chemical welding or detent.

Figure 2:
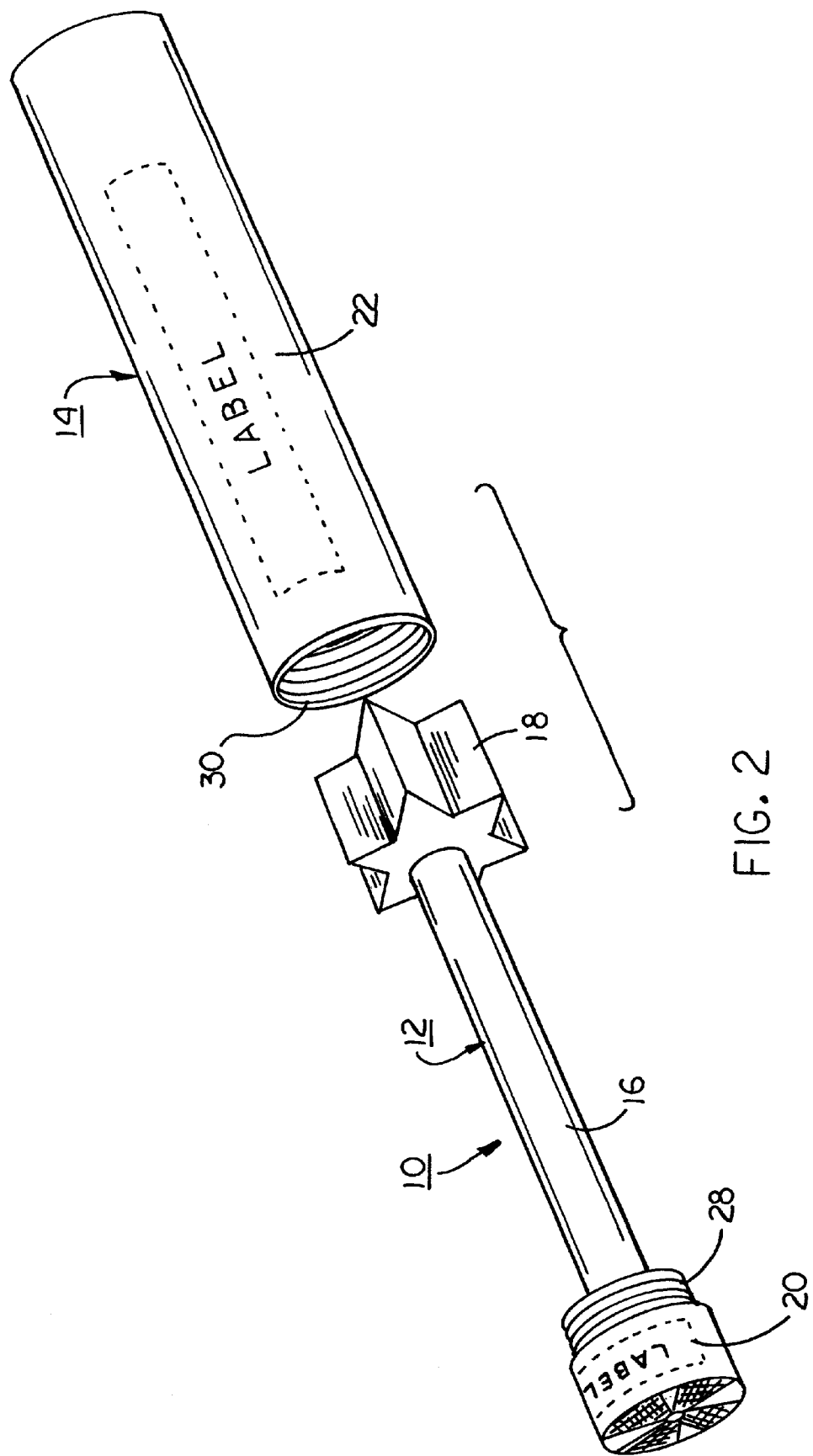
FIG. 2 is a perspective view of one embodiment of the present invention with the dotted lines indicating coordinating labels.

The form of the cap 20 may vary depending upon the sample taken. For example, as those with skill in the art are aware, if buccal cells are collected for DNA testing of paternity, the specimen must be adequately dried for the proper extraction of the DNA to prevent fungal and bacterial growth. As such, the cap should be vented to ambient air, such as shown in FIGS. 1 and 2, with vents, shown by shading, located through the cap ceiling. Preferably, for such an application, the vent should comprise at least 50% of the surface area up to any amount that is sufficient to provide enough surface area for sturdy attachment of the swab shaft. The preferred surface area comprises approximately 75% of the surface area of the cap ceiling. Also, vents may be located through the side walls of the cap.

If venting is not desired, such as with collection of cells for forensic studies, the cap would then be formed without vents to maintain sterility to the specimen once it is returned to the transport member.

Figure 3:
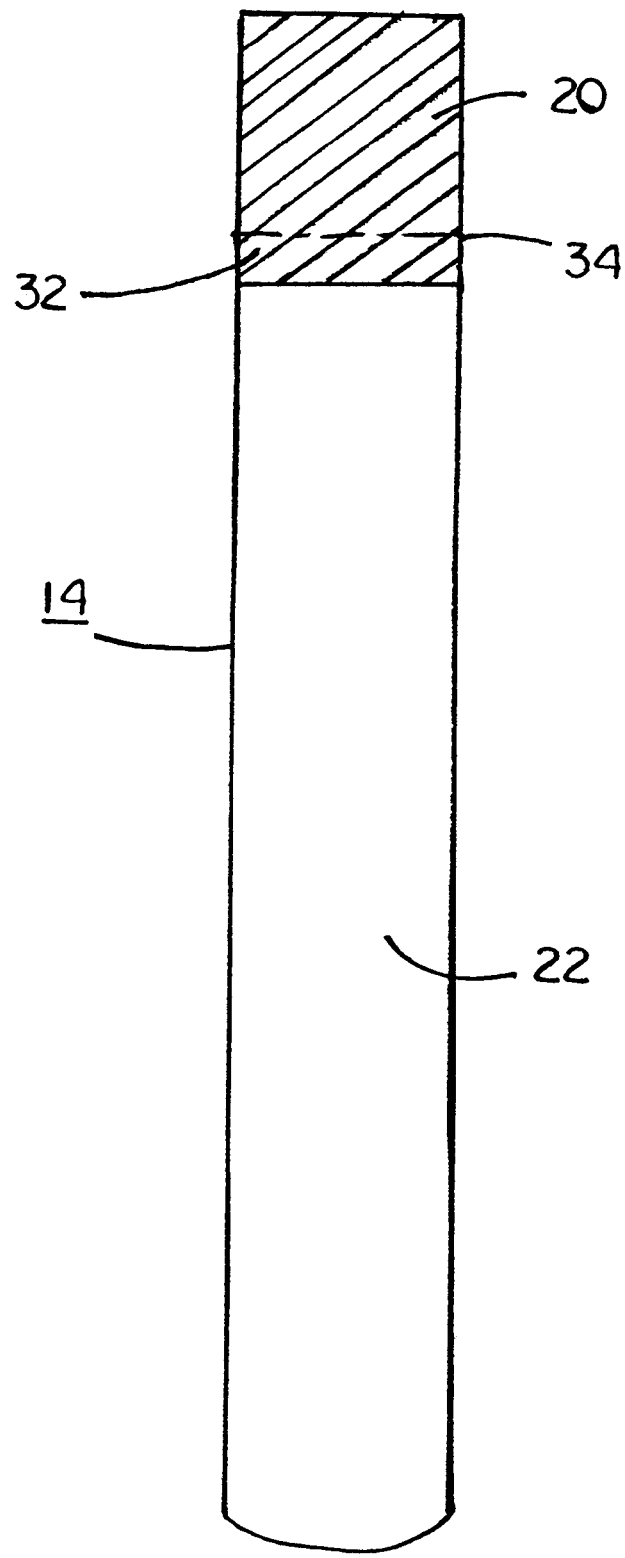
FIG. 3 is a side elevational view of one embodiment of the transport component of the present invention with shading to represent a tamper-evident seal.

With either configuration, the cap 20 preferably is covered with a tamper evident seal illustrated by shading in FIG. 3. Such seals are known in the art to ensure sterility before the specimen is taken to prevent dislocation of the cap 20 from the tube 14.

The cap 20 should be formed to fit securely upon the tube to complete the transport device. The cap 20 may be selectively securable to the tube 22 through any appropriate means, such as detent means or threaded engagement. As shown in FIG. 4, the cap 20 preferably is male-threaded 28 for union with the female-threaded 30 tube or vice-versa for transport. The tube 22, again, may be formed of any appropriate material but polypropylene is preferred because polypropylene resists breakage and provides a non-adherent surface for biological cells and cellular components. The preferred configuration of the tube 22 is round-bottomed with a clear or opaque finish. The combination of collection member 12 and transport member 14 forms the complete package.

As shown in FIG. 2, the present invention preferably includes a corresponding coordinating feature to facilitate matching identification between the collection member 12 and the transport member 14. A preferred feature is corresponding labels. As illustrated in FIG. 2 to facilitate the coordination of corresponding collection members 12 with their respective transport members 14, coordinating labels, such as bar-coding, should be affixed to the cap 20 and tube 22 of each package. Also other examples of corresponding coordinating features may be any combination of the shaft 16, foam swab 18, cap 20, and tube 22 may be color coordinated to further ensure correspondence between collection 12 and transport 14 members.

As a non-limiting example for the preferred dimensions of the present invention, the shaft 16 should be about 105 mm in height and have an about 5 mm outer diameter. The foam swab 18 should be about 18 mm in height and have an about 15 mm outer diameter. The tube 22 should be about 107 mm in height with an about 16 mm outer diameter and a cap with about a 20 mm height and about a 17 mm outer diameter.

A tamper-evident seal 32 of about 17 mm outer diameter with an approximate 10 mm long removal tab 34 should be included about the periphery of the cap 20 to seal the point of union with tube 14. Preferably the package is sterilized via radiation after the foil seal is adhered but before the culture or specimen is to be taken. The seal material may be foil, plastic, or any other appropriate material.

While the invention has been particularly shown and described with reference to a preferred embodiment thereof, it will be understood by those skilled in the art that various changes in form and details to accommodate manufacturing requirements may be made therein without departing from the spirit and scope of the invention.

What is claimed is:

1. A device for the collection of cell specimens comprising:
   (a) a shaft having a first and a second end;
   (b) a swab, said swab being affixed to the first end of the shaft; and
   (c) a tube dimensioned to receive the swab,
      wherein the tube and shaft each include a corresponding coordinating feature as to facilitate matching identification and reduce the likelihood of contamination among cell specimens.

2. The device of claim 1 further comprising:
   a cap affixed to the second end of the shaft.

3. The device of claim 2 wherein the shaft is polystyrene and the cap is polypropylene.

4. The device of claim 1 wherein the swab is formed of dental foam.

5. The device of claim 1 wherein the cross-section of the swab is a multi-pointed star.

6. The device of claim 1 wherein the cross-section of the swab is a polygon with multiple apexes.

7. The apparatus of claim 2 wherein the tube is selectively matingly engageable with the cap.

8. The apparatus of claim 7 wherein the tube is polypropylene.

9. The apparatus of claim 7 further comprising:
   coordinated labels affixed to the cap and tube.

10. The apparatus of claim 7 wherein the cap is male-threaded and engages with a female-threaded tube or vice-versa.

11. An apparatus for the collection of cell specimens comprising:
    (a) a shaft having a first and a second end;
    (b) a swab affixed to the first end of the shaft;
    (c) a cap affixed to the second end of the shaft; and
    (d) ventilation apertures within the cap, wherein the ventilation apertures comprise at least 50% of the cap surface area.

12. The apparatus of claim 11 further comprising:
    a tube of proper proportions to receive the swab and shaft that is selectively matingly engageable with the vented cap.

13. The apparatus of claim 11 wherein the ventilation apertures comprise approximately 75% of the cap surface area.

14. The apparatus of claim 12 wherein the cap and tube each have coordinating labels.

15. The apparatus of claim 12 wherein the cap has male threads and the tube has matchable female threads or vice-versa.

16. The apparatus of claim 12 further comprising:
a tamper-evident seal about the vented cap that secures the cap to the tube.

17. An apparatus for collecting and transporting cell specimens comprising:
   (a) a shaft having a first end and a second end;
   (b) a swab affixed to the first end of the shaft;
   (c) a cap affixed to the second end of the shaft, said cap having:
      (i) a label;
      (ii) ventilation apertures, wherein the ventilation apertures comprise approximately 75% of the cap surface area; and
   (d) a tube that is matingly engageable with the cap and dimensioned to receive the swab and shaft, wherein tube and cap each include a corresponding label to facilitate matching identification and reduce the likelihood of resulting contamination among cell specimens.

18. The apparatus of claim 17 wherein the swab is formed of dental foam, the cross-section of said swab being star-shaped.

19. A method for the collection of cell cultures comprising:
   (a) receiving a multi-apex swab formed of dental foam enclosed within a capped tube wherein the foam swab is attached to the cap by a shaft;
   (b) removing the cap and swab from the tube;
   (c) collecting cells;
   (d) replacing the swab within the tube; and
   (e) securing the cap onto the tube;
   (f) venting the collected cells to ambient air; and
   (g) drying the collected cells, while the swab is in the tube, for proper DNA extraction.

20. The method of claim 19 further comprising:
   (a) receiving the capped tube with a tamper-evident seal about the cap; and
   (b) breaking the seal before removal of the cap and swab.

21. The method of claim 19 wherein the capped tube and its contents are sterilized before collection.

22. An apparatus for the collection and transportation of cell specimens comprising:
   (a) a polypropylene shaft having a first and a second end;
   (b) a dental foam swab formed with a cross-sectional shape of a multi-pointed star and affixed to the first end of the shaft;
   (c) a polypropylene cap with an end wall, having vents formed through the end wall thereof wherein approximately 75% of the surface area of the cap is vents and affixed to the second end of the shaft,
   (d) a polypropylene tube of such size and shape as to house said shaft sand swab;
   (e) said cap being matingly engageable with the tube;
   (f) a tamper-evident seal adhered about the engagement of the cap and tube; and
   (g) coordinated bar-coded labels affixed to the cap and tube.

* * * * *